(12) United States Patent
Jung et al.

(10) Patent No.: US 11,628,196 B1
(45) Date of Patent: Apr. 18, 2023

(54) METHOD FOR PREPARING HEALTH FOODS COMPRISING ALOESWOOD HAVING EFFECTS OF PREVENTING ABSORPTION OF HEAVY METALS INTO BODY AND EXCRETING THE SAME FROM BODY

(71) Applicants: Jong Moon Jung, Daegu-si (KR); Kwang Ho Jung, Daegu-si (KR)

(72) Inventors: Jong Moon Jung, Daegu-si (KR); Kwang Ho Jung, Daegu-si (KR)

( * ) Notice: Subject to any disclaimer, the term of this patent is extended or adjusted under 35 U.S.C. 154(b) by 0 days.

(21) Appl. No.: 17/890,777

(22) Filed: Aug. 18, 2022

(30) Foreign Application Priority Data

Feb. 17, 2022 (KR) .................. 10-2022-0020977

(51) Int. Cl.

| | | |
|---|---|---|
| *A61K 36/835* | (2006.01) | |
| *A61K 36/78* | (2006.01) | |
| *A61K 36/11* | (2006.01) | |
| *A61K 36/82* | (2006.01) | |
| *A23L 33/105* | (2016.01) | |
| *B01D 3/06* | (2006.01) | |

(52) U.S. Cl.
CPC .......... *A61K 36/835* (2013.01); *A23L 33/105* (2016.08); *A61K 36/11* (2013.01); *A61K 36/78* (2013.01); *A61K 36/82* (2013.01); *B01D 3/06* (2013.01); *A23V 2002/00* (2013.01); *A61K 2236/13* (2013.01); *A61K 2236/15* (2013.01); *A61K 2236/17* (2013.01); *A61K 2236/55* (2013.01)

(58) Field of Classification Search
CPC ... A23L 33/105; A23V 2002/00; A61K 36/11; A61K 36/78; A61K 36/82; A61K 36/835; A61K 2236/13; A61K 2236/15; A61K 2236/17; A61K 2236/55; B01D 3/06
See application file for complete search history.

(56) References Cited

U.S. PATENT DOCUMENTS

| | | |
|---|---|---|
| 10,485,840 B1 | 11/2019 | Jung |
| 10,595,552 B2 | 3/2020 | Jung |

FOREIGN PATENT DOCUMENTS

| | | | |
|---|---|---|---|
| KR | 10-2009-0102928 A | 10/2009 | |
| KR | 101869492 B1 | 7/2018 | |
| KR | 101953366 B1 | 2/2019 | |
| KR | 102187229 B1 | 12/2020 | |
| KR | 20210148499 A | * 12/2021 | |

* cited by examiner

*Primary Examiner* — Charles S Bushey
(74) *Attorney, Agent, or Firm* — H&I Partners; C. Andrew Im; Jean-Christophe Hamann

(57) ABSTRACT

A method for preparing health foods having aloeswood. Preparing materials in which aloeswood, Saururus chinensis, Huperzia, white tea and Houttuynia cordata Thunb are each washed, and then dried in shade, pulverized and roasted. The roasted aloeswood, Saururus chinensis, Huperzia, white tea and Houttuynia cordata Thunb are mixed at a weight ratio of 4:1:1:1:1. The brewed and distilled aloeswood, Saururus chinensis and water mixture is mixed with the maturing an aloeswood, Saururus chinensis, Huperzia, white tea and Houttuynia cordata Thunb mixture and double boiled to prepare a leachate. The prepared leachate is extracted and concentrated, and then heat-matured to remove the moisture. The heat-matured extract is cool-dried, mixed with mineral water, then heated, dried at room temperature and molded into a predetermined shape. The prepared health foods having effects in preventing absorption of heavy metals in body and excreting the same from body.

4 Claims, No Drawings

METHOD FOR PREPARING HEALTH FOODS COMPRISING ALOESWOOD HAVING EFFECTS OF PREVENTING ABSORPTION OF HEAVY METALS INTO BODY AND EXCRETING THE SAME FROM BODY

RELATED APPLICATION

The present application claims priority from Korean Patent Application No. 10-2022-0020977 filed Feb. 17, 2022, which is incorporated herein by reference in its entirety.

FIELD OF THE INVENTION

The present invention relates to a method for preparing health foods comprising aloeswood having effects of preventing absorption of heavy metals into body and excreting the same from body, more specifically, a method for preparing health foods comprising aloeswood having effects of preventing absorption of heavy metals into body and excreting the same from body, wherein the health foods comprise aloeswood having anti-inflammatory, antiviral, anti-allergic, antispasmodic, analgesic, sedative effects, physical recovery and health promotion effects and so on; and Saururus chinensis having effects on the treatment of heavy metal ingredients to provide effects that are beneficial to body and at the same time, to detox heavy metals.

BACKGROUND OF THE RELATED ART

The development of industrial society has made life convenient, while environmental contamination caused thereby is threatening the living environment of humans. Of the environmental contaminations, the contamination of soil or water can cause acute or chronic poisoning, as the heavy metals are transported to and accumulated in human body.

When some types of heavy metals form organic or inorganic compounds, their transport in the body become easy, giving various adverse effects.

In particular, once introduced in the body, heavy metals are not easily excreted, and as the accumulation increases, they cause poisoning, which includes weight decrease, anemia, biochemical and morphological deformation of organs, and brain damage. In addition, heavy metals operate competitively with essential mineral elements, such as calcium, iron, zinc and selenium, in the step of absorption to the gut, decreasing their contents in the tissues. In addition, some toxic metals react with body tissues even at a relatively low concentration, and gradually exhibit toxic actions in the body. In particular, because heavy metals have a long biological half-life, once poisoned, the poisoning may not be completely cured.

Due to the social background, as a part of the studies to mitigate the symptoms of lead and cadmium poisoning, the effects of cellulose, selenium and trace elements have been studied, and there is a report that catechin in black tea and green tea improved the renal function disorders caused by cadmium poisoning and normalized blood pressure.

In addition, when a hazardous material is introduced to a body, biotransformation occurs in the body to rapidly excrete the hazardous material, and as a result, the hazardous material is excreted from the body through the action.

The metabolic process is described in two phases: foreign materials, such as the environmental contaminants or drugs that are absorbed into the body, are excreted from the body by either phase 1 reaction or phase 2 reaction in the liver tissues or through both phases.

Phase 1 enzyme, including cytochrom P450, modifies hydrophobic compounds to have reactive electrons through oxidation, reduction and hydrolysis reactions, converting the hydrophobic compounds into highly reactive compounds. Phase 2 enzyme, including glutathione S-transferase, UDP-glucuronosyltransferase and quinone reductase, converts highly metabolic materials into stable materials so that they can be easily excreted (Liska DJ. Alter med rev 3: 187 -198, 1998).

Recently, many studies have been conducted on the correlation of glucosinolates, which are sulfur-containing substances of Cruciferae vegetables such as cauliflower, cabbage, kale and broccoli, as potential cancer-preventing substances, with cancers, and the results showed that glucosinolates have an anticancer activity because they changed the expression of a biotransformation enzyme.

As described above, studies have been actively conducted on the anticancer activity in relation with the induction of the phase 1 or phase 2 enzymatic activity, but studies on the detoxification of heavy metal materials by the substances and the relevant scientific data are relatively insufficient. In addition, little has been studied about the food resources that can prevent the accumulation of heavy metals in the body and induce their excretion from the body.

In a study on a composition that can mitigate the damage by the poisoning of lead and cadmium, which are hazardous heavy metals, it was confirmed that natural plants comprising Saururus chinensis and aloeswood have a significant effect of detoxicating heavy metals and that the plants can be used as health foods for detoxicating heavy metals. Therefore, the invention recited in the present application was completed.

Prior Arts

Cited Document D1: KR 10-2009-0102928 (published on Oct. 1, 2009)

SUMMARY AND OBJECT OF THE INVENTION

The invention recited in the present application, invented to overcome the abovementioned problem, provides a method for preparing health foods comprising aloeswood that, when ingested, facilitate the absorption of hazardous heavy metals in body and the excretion of the same from body and that exhibit anti-inflammatory, antiviral, anti-allergic, antispasmodic, analgesic, sedative effects, physical recovery and health promotion effects and so on.

The present application relates to a method for preparing health foods comprising aloeswood, the method comprising:

preparing materials in which aloeswood, Saururus chinensis, Huperzia, white tea and Houttuynia cordata Thunb. are each washed, and then dried in shade;

pulverizing in which, after the preparing materials is completed, each material is pulverized by using a pulverizer;

roasting in which, after the pulverizing is completed, each pulverized material is roasted in a cauldron heated to 90 to 120° C. for 1 to 2 minutes and then cooled to sterilize the materials and enhance fragrances;

maturing an aloeswood, Saururus chinensis, Huperzia, white tea and Houttuynia cordata Thunb. mixture in which, after the roasting is completed, the roasted aloeswood, Saururus chinensis, Huperzia, white tea and Houttuynia cordata Thunb. are mixed at a weight ratio of 4:1:1:1:1 and then sealed and matured for 6 to 8 days;

preparing an aloeswood and Saururus chinensis mixture in which a mixture is prepared by mixing aloeswood and Saururus chinensis at a weight ratio of 1:1;

brewing in which the aloeswood and Saururus chinensis mixture is added, based on 100 parts by weight of the aloeswood and Saururus chinensis mixture, to 4,000 to 12,000 parts by weight of water, and then boiled at a temperature range of 70 to 90° C. for 22 to 26 hours;

maturing the aloeswood and Saururus chinensis mixture in which, after the brewing is completed, the aloeswood and Saururus chinensis mixture is cooled to room temperature and then matured at a temperature range of 18 to 22° C. for 22 to 26 hours;

distilling under reduced pressure in which, after the maturing the aloeswood and Saururus chinensis mixture is completed, distilling under reduced pressure is performed;

preparing a leachate in which the aloeswood and Saururus chinensis mixture that has undergone the distilling under reduced pressure is mixed with the mixture that has undergone the maturing an aloeswood, Saururus chinensis, Huperzia, white tea and Houttuynia cordata Thunb. mixture at a weight ratio of 1:1 to 1:3, and the resulting mixture is put into a double boiler and double boiled at a temperature range of 83 to 85° C. for 15 to 20 hours to prepare a leachate;

extracting in which, after the preparing a leachate is completed, the prepared leachate is put into an extractor and heated at a temperature range of 150 to 180° C. for 10 to 15 hours under a pressure of 3 to 4 kgf/cm$^2$ to extract;

concentrating in which an extract obtained after the extracting is completed is put into the extractor again and heated under a pressure of 4 to 4.5 kgf/cm$^2$ for 2 to 4 hours to concentrate the extract;

heat-maturing in which a concentrate obtained after the concentrating is completed is heated at a temperature range of 95 to 100° C. for 6 to 8 hours to mature the concentrate by removing moisture;

cool-drying the concentrate in which the concentrate obtained after the heat-maturing is completed is dried at a temperature range of 5 to 8° C. until the moisture content becomes 14 to 16 wt %;

heating the concentrate in which the concentrate that has undergone the cool-drying of a concentrate is put into, based on 100 parts by weight of the concentrate, 100 to 300 parts by weight of mineral water, and then heated at a temperature range of 90 to 98° C. for 5 to 20 minutes;

drying the concentrate in which the concentrate, after the heating the concentrate is completed, is dried at room temperature; and molding in which the concentrate, after the drying the concentrate is completed, is molded to a predetermined shape.

The invention recited in the present application, invented to overcome the abovementioned problem, provides a method for preparing health foods comprising aloeswood that, when ingested, facilitate the absorption of hazardous heavy metals in body and the excretion of the same from body and that exhibit anti-inflammatory, antiviral, antiallergic, antispasmodic, analgesic, sedative effects, physical recovery and health promotion effects and so on.

DETAILED DESCRIPTION OF THE EMBODIMENTS

The present invention is specifically described below.

One aspect of the present invention provides a method for preparing health foods comprising aloeswood, the method comprising: preparing materials in which aloeswood, Saururus chinensis, Huperzia, white tea and Houttuynia cordata Thunb. are each washed, and then dried in shade; pulverizing in which, after the preparing materials is completed, each material is pulverized by using a pulverizer; roasting in which, after the pulverizing is completed, each pulverized material is roasted in a cauldron heated to 90 to 120° C. for 1 to 2 minutes and then cooled to sterilize the materials and enhance fragrances; maturing an aloeswood, Saururus chinensis, Huperzia, white tea and Houttuynia cordata Thunb. mixture in which, after the roasting is completed, the roasted aloeswood, Saururus chinensis, Huperzia, white tea and Houttuynia cordata Thunb. are mixed at a weight ratio of 4:1:1:1:1 and then sealed and matured for 6 to 8 days; preparing an aloeswood and Saururus chinensis mixture in which a mixture is prepared by mixing aloeswood and Saururus chinensis at a weight ratio of 1:1; brewing in which the aloeswood and Saururus chinensis mixture is added, based on 100 parts by weight of the aloeswood and Saururus chinensis mixture, to 4,000 to 12,000 parts by weight of water, and then boiled at a temperature range of 70 to 90° C. for 22 to 26 hours; maturing the aloeswood and Saururus chinensis mixture in which, after the brewing is completed, the aloeswood and Saururus chinensis mixture is cooled to room temperature and then matured at a temperature range of 18 to 22° C. for 22 to 26 hours; distilling under reduced pressure in which, after the maturing the aloeswood and Saururus chinensis mixture is completed, distilling under reduced pressure is performed; preparing a leachate in which the aloeswood and Saururus chinensis mixture that has undergone the distilling under reduced pressure is mixed with the mixture that has undergone the maturing an aloeswood, Saururus chinensis, Huperzia, white tea and Houttuynia cordata Thunb. mixture at a weight ratio of 1:1 to 1:3, and the resulting mixture is put into a double boiler and double boiled at a temperature range of 83 to 85° C. for 15 to 20 hours to prepare a leachate; extracting in which, after the preparing a leachate is completed, the prepared leachate is put into an extractor and heated at a temperature range of 150 to 180° C. for 10 to 15 hours under a pressure of 3 to 4 kgf/cm$^2$ to extract; concentrating in which an extract obtained after the extracting is completed is put into the extractor again and heated under a pressure of 4 to 4.5 kgf/cm$^2$ for 2 to 4 hours to concentrate the extract; heat-maturing in which a concentrate obtained after the concentrating is completed is heated at a temperature range of 95 to 100° C. for 6 to 8 hours to mature the concentrate by removing moisture; cool-drying the concentrate in which the concentrate obtained after the heat-maturing is completed is dried at a temperature range of 5 to 8° C. until the moisture content becomes 14 to 16 wt %; heating the concentrate in which the concentrate that has undergone the cool-drying of a concentrate is put into, based on 100 parts by weight of the concentrate, 100 to 300 parts by weight of mineral water, and then heated at a temperature range of 90 to 98° C. for 5 to 20 minutes; drying the concentrate in which the concentrate, after the heating the concentrate is completed, is dried at room temperature; and molding in which the concentrate, after the drying the concentrate is completed, is molded to a predetermined shape.

In the method for preparing health foods according to one aspect of the present invention, particularly, the method for preparing health foods comprising aloeswood having effects in preventing absorption of heavy metals in body and excreting the same from body, the materials used comprises aloeswood, Saururus chinensis, Huperzia, white tea and Houttuynia cordata Thunb.

Here, the leaf of aloeswood, Saururus chinensis, Huperzia, white tea and Houttuynia cordata Thunb. can preferably be used, but not limited thereto, and the root and stem thereof can also be used.

The aloeswood according to one aspect of the present invention is formed by the solidification of the resin of ever-green tall trees of Thymelaeaceae that naturally grow in Southeast Asia.

The aloeswood is formed by burying juniper and oak trees at a harbor confluence of sea water and mountainous valley water streams, as various mineral ingredients contained in the sea water and mountainous valley water infiltrate into the trees for a long time, and so the aloeswood herein refers to solid aloeswood that sinks in water in contrast to general wood.

Furthermore, the aloeswood according to one aspect of the present invention is, more specifically, aloeswood formed by the solidification of resin on an aloeswood tree, and any common aloeswood that is permitted to drink in the art can be used.

In particular, the aloeswood according to one aspect of the present invention has supreme fragrance and is rich with monoterpene, terpene, and sesquiterpene-based substances, thus exhibiting anti-allergic, antispasmodic, analgesic, sedative effects, helping physical recovery and health promotion, and providing pharmaceutical effects such as anti-cancer, anti-inflammatory and antiviral effects.

Saururus chinensis according to one aspect of the present invention is a perennial plant of Dicotyledoneae Piperales Saururaceae. The rhizome is white and laterally stretches in mud. The height of the stem is 50 to 100 cm, and a white flower blooms in June to August. Saururus chinensis usually grows in a wetland, and has a nickname Sambaekcho,' meaning 'grass with three whites,' because the root, leaf and flower are white. Saururus chinensis is known to have medical effects on beriberi, jaundice and hepatitis, and found in Korea, Japan, China and so on.

Since Saururus chinensis clarifies blood and cleanses vascular walls, it has an effect of preventing and treating heart disorders, hypertension and cardiac diseases such as angina. Saururus chinensis also enhances the detoxicating function of liver and thus improves the renal functions. Saururus chinensis also enhances the functions of kidneys to treat renal inflammation. In addition, Saururus chinensis, containing quercetin and isoflavone, can prevent cancers or adult diseases, and at the same time, remove tumors in body and eliminate lipoperoxide that is generated by the aging of human body.

Any Saururus chinensis that is common in the art can be used as the Saururus chinensis according to one aspect of the present invention can be, but preferably, yellow ocher Saururus chinensis can be used.

Here, the yellow ocher Saururus chinensis refers to the native naturally growing plant designated as the Endangered Plant No. 177. The plant grows very strongly and is clan without free from harmful insects. The plant is called by the nickname 'Cheonseongcho,' and its marvelous effects are written in Bonchogangmok, Encyclopedia of Chinese Herbal Medicines and Dongeuibogam.

In particular, the Saururus chinensis according to one aspect of the present invention comprises flavone-based substances, water-soluble tannin, essential amino acids and effective minerals. In particular, the stem contains a large amount of water-soluble tannin; the leaf contains a large amount of quercetin, quercitrin, isoquercitrin, avicularin, hyperin, lucin and water-soluble tannin; and the root contains various amino acids and effective minerals.

Here, the water-soluble tannin has excellent anti-cancer, antioxidant and anti-aging effects with a diuretic effect, and it binds to an enzyme in the body to burn off body fat and exhibit anti-inflammatory and anti-swelling effects as well as a detoxicating effect; the quercetin, quercitrin, isoquercitrin, avicularin, hyperin, lucin and water-soluble tannin exhibit effects of preventing and treating hypertension and stroke; and the flavone-based substances and water-soluble tannin increase the elasticity of peripheral blood vessels to help peripheral arterial circulation, and have diuretic and spleen-enhancing actions to prevent diseases and aging.

In particular, the water-soluble tannin, having the above-mentioned effects, has the characteristic of easily binding to heavy metals in water. Therefore, tannin is bound to mercury or cadmium, which is a heavy metal, to form tannin mercury or tannin cadmium so that the hazardous heavy metal components may not be dissolved in the blood but be excreted out of the body, protecting our body. Moreover, tannin is capable of preventing peroxidation of cells in the body and thus has the effect of strengthening pancreatic cells, preventing diabetes.

Huperzia according to one aspect of the present invention is a perennial ever-green plant of Lycopodiopsida, Lycopodiales and Lycopodiaceae. Any common Huperzia in the art can be used.

Here, the Huperzia comprises sesquiterpene and so plays the role of preserving the fragrance of aloeswood.

An white tea that is common in the art can be used as the white tea according to one aspect of the present invention, but preferably, white tea leaf can be used.

Here, as the white tea leaf, tea shoots covered with soft fine hairs can be used without wiping or rubbing to brew tea.

In particular, shoots of white tea covered with soft fine hairs has silver gloss, clear fragrance and fresh taste.

White tea removes lipids, induces smooth urination, and cleanses the intestines. In addition, white tea is good to patients with diabetes, and is used as a herbal medicine as it can reduce heat in summer.

The Houttuynia cordata Thunb. according to one aspect of the present invention is a perennial herb of Saururaceae, and refers to a plant head with the root of Houttuynia cordata Thunb. The whole plant head with the root is plucked up in summer and autumn for utilization. The plant contains essential oil including decanoyl acetaldehyde, methyl-n-nonyl-ketone, a-pinene, linalool and d-limonen, as antibacterial components, and it also contains cordarine. Reports have shown that the plant has antiviral and diuretic effects.

The materials used in the method for preparing health foods comprising aloeswood according to one aspect of the present invention, having the features described above, particularly, in the method for preparing health foods comprising aloeswood having effects in preventing absorption of heavy metals in body and excreting the same from body, particularly, aloeswood, Saururus chinensis, Huperzia, white tea and Houttuynia cordata Thunb. are cleanly washed, and then dried in shade to prepare health foods.

The materials according to one aspect of the present invention, including aloeswood, Saururus chinensis, Huperzia, white tea and Houttuynia cordata Thunb., are preferably used, after being dried, in the form of powder. In this case, pulverizing performed by using a pulverizer or the ball-mill method is recommended.

Here, in the pulverizing, it is good that each material has a mean diameter in a range of 0.1 to 3.0 mm.

The roasting according to one aspect of the present invention comprises roasting each of the pulverized materials in a cauldron heated to 90 to 120° C. for 1 to 2 minutes and then cooling to sterilize the materials and enhance fragrances.

The maturing according to one aspect of the present invention comprises, particularly, the maturing an aloeswood, Saururus chinensis, Huperzia, white tea and Houttuynia cordata Thunb. mixture comprises mixing, after the roasting is completed, the roasted aloeswood, Saururus chinensis, Huperzia, white tea and Houttuynia cordata Thunb. preferably at a weight ratio of 4:1:1:1:1 and then sealed and matured for 6 to 8 days.

The preparing aloeswood and Saururus chinensis mixture according to one aspect of the present invention comprises preparing a mixture by mixing aloeswood and Saururus chinensis at a weight ratio of 1:1.

Here, the aloeswood and Saururus chinensis mixture is for treating heavy metal components and improving the effect of aloeswood, wherein the Saururus chinensis can provide effects of preventing the absorption of heavy metals in body and excreting the same from body.

The brewing mixture according to one aspect of the present invention comprises adding the aloeswood and Saururus chinensis mixture is added, based on 100 parts by weight of the aloeswood and Saururus chinensis mixture, to 4,000 to 12,000 parts by weight of water, preferably about 10,000 parts by weight (10 L), and boiling at a temperature range of 70 to 90° C., preferably at a temperature about 80 ° C. for 22 to 26 hours, preferably, 24 hours.

The maturing the aloeswood and Saururus chinensis mixture according to one aspect of the present invention comprises cooling, after the brewing is completed, the aloeswood and Saururus chinensis mixture to room temperature and then maturing at a temperature range of 18 to 22° C., preferably at 20 ° C., for 22 to 26 hours, preferably, 24 hours.

The distilling under reduced pressure according to one aspect of the present invention comprises distilling, after the maturing the aloeswood and Saururus chinensis mixture is completed, the matured aloeswood and Saururus chinensis mixture.

Here, any common method for distilling under reduced pressure in the art can be used as the method for distilling under reduced pressure.

Here, performing the method for distilling under reduced pressure by using an automated mechanical equipment facility (distillation facility) is recommended.

The preparing a leachate according to one aspect of the present invention comprises mixing the aloeswood and Saururus chinensis mixture that has undergone the distilling under reduced pressure with the mixture that has undergone the maturing an aloeswood, Saururus chinensis, Huperzia, white tea and Houttuynia cordata Thunb. mixture at a weight ratio of 1:1 to 1:3, putting the resulting mixture into a double boiler, and double-boiling at a temperature range of 83 to 85° C. for 15 to 20 hours to prepare a leachate.

The extracting according to one aspect of the present invention comprises putting, after the preparing a leachate is completed, the prepared leachate into an extractor and heating at a temperature range of 150 to 180° C. for 10 to 15 hours under a pressure of 3 to 4 kgf/cm$^2$ to extract.

The concentrating according to one aspect of the present invention comprises putting an extract obtained after the extracting is completed into the extractor again and heated under a pressure of 4 to 4.5 kgf/cm$^2$ for 2 to 4 hours to concentrate the extract.

The heat-maturing according to one aspect of the present invention comprises heating a concentrate obtained after the concentrating is completed at a temperature range of 95 to 100° C. for 6 to 8 hours to mature the concentrate by removing moisture.

The cool-drying the concentrate according to one aspect of the present invention comprises drying the concentrate obtained after the heat-maturing is completed at a temperature range of 5 to 8° C. until the moisture content becomes 14 to 16 wt %.

The heating the concentrate according to one aspect of the present invention comprises putting the concentrate that has undergone the cool-drying of a concentrate into, based on 100 parts by weight of the concentrate, 100 to 300 parts by weight of mineral water, and then heating at a temperature range of 90 to 98° C. for 5 to 20 minutes.

The drying the concentrate according to one aspect of the present invention comprises drying, after the heating the concentrate is completed, the concentrate at room temperature.

Here, the method for preparing health foods comprising aloeswood according to one aspect of the present invention comprises preparing a concentrate and honey mixture, following the drying the concentrate, in which the dried concentrate is mixed with, based on 100 parts by weight of the concentrate, 2,500 to 3,500 parts by weight of honey.

Here, the honey is used to make the finally molded health foods more convenient for eating.

The molding according to one aspect of the present invention comprises molding the concentrate, after the drying the concentrate is completed, to a predetermined shape, for example, in the form of pills, tablets, gel and so on.

The method for preparing health foods comprising aloeswood having effects of preventing absorption of heavy metals into body and excreting the same from body may further comprise one or more than one additive according to the embodiment of the present invention described below.

According to one embodiment of the present invention, the method for preparing health foods comprising aloeswood according to one aspect of the present invention, more specifically, the method for preparing health foods comprising aloeswood having effects of preventing absorption of heavy metals into body and excreting the same from body may further comprise in the preparing a leachate, 3 to 7 parts by weight of a Adenophola triphylla and Pueraria extract mixture, prepared by mixing Adenophola triphylla and Pueraria at a weight ratio of 1:1, based on 100 parts by weight of the aloeswood and Saururus chinensis mixture.

The Adenophola triphylla, referring to the root of ladybell, is cold in nature, tastes sweet, is nontoxic, and has an excellent detoxicating effect, and has been known to have an effect of treating snake bite or insect bite. The Adenophola triphylla is also known as having excellent effects of quickly healing a wound, removing hangover and recovering from fatigue. The fresh juice from the raw material is difficult to drink due to the disgusting taste. Pueraria has a unique taste, and so some people may have resistance to it. Therefore, it is good to extract these materials and use the extract mixture.

The Adenophola triphylla and Pueraria extract mixture according to one aspect of the present invention, prepared by mixing at a weight ratio of 1:1, can be obtained from the following process: first immersion process in which Adenophola triphylla and Pueraria are each immersed in water for 3 to 5 hours; second immersion process in which the Adenophola triphylla and Pueraria that have undergone the first immersion process are washed and then each immersed again in water for 3 to 5 hours; boiling down process in which the Adenophola triphylla and Pueraria that have undergone the second immersion process are mixed with each other at a weight ratio of 1:1 and then mixed with water, and the resulting mixture is heated until the amount of water is reduced to ½ or ⅔; dehydration process in which the Adenophola triphylla and Pueraria that have completed the boiling down process are squeezed through a dehydrator to produce a juice; and a heat-mixing process in which the water remaining after the boiling down process and the juice obtained through the dehydration process are mixed, and the resulting mixture is heated at a temperature of 100 ° C. for 10 to 30 minutes and then cooled to room temperature.

Here, the Adenophola triphylla and Pueraria can be softened to be ingested as a general beverage through the first immersion process and the second immersion process. Therefore, the Adenophola triphylla and Pueraria from which impurities are considerably removed and which are not fully softened through the first immersion process are subject to the second immersion process to remove the remaining impurities and to seek further softening. In addition, the heat-mixing process is performed to appropriately mix the Adenophola triphylla and Pueraria extract and remove bacteria therefrom.

According to another embodiment of the present invention, the method for preparing health foods comprising aloeswood according to one aspect of the present invention may further comprise in the preparing a leachate, 3 to 7 parts by weight of a cockscomb fermentation product, based on 100 parts by weight of the aloeswood and Saururus chinensis mixture.

The cockscomb is an annual plant of dicotyledon, Centrospermales and Amaranthaceae, and it has a cold nature and tastes bitter. The cockscomb is known to have the effects of reaching the liver and large intestines to calm down inflammation and stop hemorrhage and diarrhea through the cold and bitter nature. Bonchogangmok also includes the record that it is good to boil the roasted cockscomb seeds and ingest the boiled water to stop leucorrhea, menstruation or diarrhea of women. The fruit, flower, leaf, stem or a mixture thereof can be used as the cockscomb. The cockscomb fermentation product, which is prepared through a fermentation process to remove the bitter taste and increase the effects, is prepared by the preparation process described below.

First, the cockscomb is pulverized to a size of 0.5 to 5 mm, and the pulverized cockscomb is mixed with sugar at a weight ratio of 50:40.

The cockscomb is pulverized to a size of 0.5 to 5 mm so that sugar can be uniformly mixed with cockscomb, and the weight ratio of cockscomb and sugar is set to be 50:40 to prevent excessive mixing of sugar, which can make the sweet taste too strong, and to prevent solid matters of the cockscomb from becoming too soft.

Then, after the sugar is sufficiently melt to permeate into the cockscomb mixed with sugar, the resulting mixture is transported to an earthen jar.

Then, the mouth of the earthen jar is covered and sealed with cotton cloth, and the mixture is fermented for about 6 months and then solid matters are filtered.

According to another embodiment of the present invention, the method for preparing health foods comprising aloeswood according to one aspect of the present invention may further comprise in the preparing a leachate, 3 to 7 parts by weight of enzyme-decomposed tangerine powder, based on 100 parts by weight of the aloeswood and Saururus chinensis mixture.

The tangerine is a variety of Aurantioideae Citrus. Tangerine contains a large amount of flavonoids and thus is known to have excellent effects of enhancing peripheral vessels, lowering blood pressure and decreasing blood cholesterols as well as anti-inflammatory and antiviral actions. However, although a large portion of the functional ingredients contained in the tangerine are contained in the fruit skin, most fruit skin is treated as waste during the processing. Therefore, enzyme-decomposed tangerine powder can be prepared by using the whole tangerine together with the fruit skin and a decomposition enzyme to free flavonoids contained in the fruit skin of the tangerine, such as hesperidin and naringin. Since the enzyme-decomposed tangerine powder contains much more functional substances, compared with the case of using the flesh of the tangerine only, the effects can be enhanced. The preparation process is described below.

First, tangerine is sterilized with a cleaning agent for microbial sterilization, washed with flowing water, and pulverized by using a wet pulverizer with the fruit skin together. Then, the resulting tangerine is transported to an enzyme-decomposer in which pectinase is added at a concentration of 200 ppm to perform enzyme-decomposition at 25° C. at a rate of 100 rpm for 3 hours. Then, the enzyme-decomposed product is separated into juice and flesh by using a filter press, and the flesh is freeze-dried and the pulverized to prepare enzyme-decomposed tangerine powder.

Here, any cleaning agent for microbial sterilization used in the technical field can be used as the cleaning agent for microbial sterilization, and pectinase is a decomposition enzyme for decomposing pectin of tangerine.

According to another embodiment of the present invention, the method for preparing health foods comprising aloeswood according to one aspect of the present invention may further comprise in the preparing a leachate, 3 to 7 parts by weight of Dendropanax morbifera leaf powder, based on 100 parts by weight of the aloeswood and Saururus chinensis mixture.

The Dendropanax morbifera is a broad-leaved ever-green tall tree that naturally grows in the south coast areas of Korea. Making a wound on the skin of the tree causes a flow of liquid resin, which is referred to as 'huangchil.' Dendropanax morbifera is known to mitigate symptoms of jaundice and be effective on burns. In particular, the leaf extract of Dendropanax morbifera is known to have good anti-cancer and immune activity. The Dendropanax morbifera leaf can be steamed and pulverized to increase the effects, and the preparation process is described below.

First, Dendropanax morbifera leaf is cleanly washed with water. Then, the leaf is cut into a size of 1 cm, and added to a steamer to steam at 100° C. for 10 minutes. Then, the leaf is dried in a hot-air dryer at 50° C. for 4 minutes. Then, the leaf is put into a pulverizer to prepare power.

Here, Dendropanax morbifera leaf is washed with water to remove impurities, and steaming and drying are performed to prevent the leak of active ingredients of Dendropanax morbifera leaf and concentrate the same.

According to another embodiment of the present invention, the method for preparing health foods comprising aloeswood according to one aspect of the present invention may further comprise in the preparing a leachate, 3 to 7 parts by weight of Poria cocos extract, based on 100 parts by weight of the aloeswood and Saururus chinensis mixture.

The Poria cocos is a white-colored mushroom of Basidiomycetes Polyporaceae, and can be used to properly control sweat, enhance urination, and treat diarrhea and so on. The Poria cocos comprises β-pachyman and contains many proteins, glucose and so on. The Poria cocos has effects on symptoms of urination difficulty and swelling of the abdomen and whole body, and is effective on the treatment of chronic cough, vomiting, diarrhea, amnesia and ganacratia. In addition, the Poria cocos exhibit a significant response to renal edema, has an effect of preventing ulcer formation, and has functions of dropping blood sugar level and inhibiting contact dermatitis. The preparation process is described below.

First, Poria cocos is cleanly washed with water, and then put into a double boiler to double-boil at a temperature of 80° C. for 18 hours. Then, the leachate was put into an extractor and heated at a temperature of 150° C. and under a pressure of 4 kgf/cm² for 12 hours to prepare the extract.

Here, Poria cocos is washed with water to remove impurities, and Poria cocos is double-boiled and extracted to prepare a Poria cocos extract in order to concentrate and extract the active ingredients of Poria cocos.

According to another embodiment of the present invention, the method for preparing health foods comprising aloeswood according to one aspect of the present invention may further comprise in the preparing a leachate, 5 to 15 parts by weight of Huperzia serrata extract, based on 100 parts by weight of the aloeswood and Saururus chinensis mixture.

Here, the Huperzia serrata is used after washing, drying in shade, pulverizing, roasting for 1 or 2 minutes in a caldron heated at 90 to 120° C., and then cooling.

The Huperzia serrata, a herbal medicine that has a long history, is introduced in various medical books in China and other countries, and has the characteristics of an antiacetylcholinesterase.

Here, the antiacetylcholinesterase, having an effect of treating and preventing dementia, has been positively used since 1980s in many countries worldwide, and is used in China for Alzheimer's disease, and recently found as having the beneficial effect of improving cognitive functions.

Furthermore, the Huperzia serrata, a herbal medicine institute in France recently visited Vietnam, the country of origin, to use the herb as an agent for preventing and treating dementia.

According to another embodiment of the present invention, the method for preparing health foods comprising aloeswood according to one aspect of the present invention may further comprise in the preparing a leachate, 3 to 12 parts by weight of vegetable worm, based on 100 parts by weight of the aloeswood and Saururus chinensis mixture.

Here, the vegetable worm is used after washing, drying in shade, pulverizing, and roasting for 1 or 2 minutes in a caldron heated at 90 to 120° C., and then cooling.

The vegetable worm is a health food produced from highland areas in China and Tibet over about 4,000 m from the sea level, and it has a superb pharmaceutical effect.

According to another embodiment of the present invention, the method for preparing health foods comprising aloeswood according to one aspect of the present invention may further comprise in the preparing a leachate, 3 to 12 parts by weight of Chinese artichoke, based on 100 parts by weight of the aloeswood and Saururus chinensis mixture.

Here, the Chinese artichoke is used after washing, drying in shade, pulverizing, and roasting for 1 or 2 minutes in a caldron heated at 90 to 120° C., and then cooling.

The Chinese artichoke has long been used as an alternative of vegetable worm which is a famous nutritious tonic, because they have a similar shape and a similar pharmaceutical effect. The Chinese artichoke is useful to prevent aging, increase metal capacity, prevent senile dementia and cerebral infarction, and treat adult diseases and chronic diseases.

In particular, with regard to the Chinese artichoke, Dr. Yamahara Joji's research group in Japan performed an experiment of injecting potassium cyanide and scientifically showed that Chinese artichoke has a function of activating brain cells, and published that phenylethanoid, a glycoside contained therein, has an effect of preventing cerebral infarction and senile dementia and increasing memory.

In addition, China has shown the Chinese artichoke tastes slight and clean and has the effects of expelling stroke, releasing extravasated blood, lowering a high energy level, healing arthritis, neuralgia, paralysis, stroke, systemic bone pain and eye diseases, and improving the liver to treat eye diseases and jaundice.

According to another embodiment of the present invention, the method for preparing health foods comprising aloeswood according to one aspect of the present invention may further comprise in the preparing a leachate, 3 to 8 parts by weight of Agrimonia eupatoria, based on 100 parts by weight of the aloeswood and Saururus chinensis mixture.

Here, the Agrimonia eupatoria is used after washing, drying in shade, pulverizing, and roasting for 1 or 2 minutes in a caldron heated at 90 to 120° C., and then cooling.

The Agrimonia eupatoria contains agrimoniin, agtrimonite, tannin, organic acids, saponin, and vitamin C and vitamin K as the key ingredients, wherein the tannin is contained in a content of about 8.9% in the root, about 6.5% in the stem, and about 16.4% in the leaf.

The Agrimonia eupatoria is a herb having excellent nutritious tonic and anti-cancer properties as well as a stamina herb. Various prescription records show that the Agrimonia eupatoria is effective on anemia and energy weakness as well as tuberculosis and hemoptysis and can treat 9 out of 10 people who have the symptoms of dysphagia and regurgitation, being unable to ingest foods (including the symptoms of stomach cancer in the late stage).

In particular, the Agrimonia eupatoria has a selective pharmaceutical function to kill cancer cells 100% and enhance the growth of normal cells.

According to another embodiment of the present invention, the method for preparing health foods comprising aloeswood according to one aspect of the present invention may further comprise in the preparing a leachate, 5 to 15 parts by weight of Lycopus lucidus Turcz, based on 100 parts by weight of the aloeswood and Saururus chinensis mixture.

Here, the Lycopus lucidus Turcz is used after washing, drying in shade, pulverizing, and roasting for 1 or 2 minutes in a caldron heated at 90 to 120° C., and then cooling.

The Lycopus lucidus Turcz is a perennial herb that is referred to as by the nicknames such as horan (Sinnongbonchogyeong), hobu (Myeongeuibyeolrok), sotaekran (Noigongpoguron), honggaekcho (Jinnamboncho), pungyak (Bonchgangmok), bodusacho (Yeongnamchaeyakrok), jeopgocho (Sikmulmyeonghoi), jirryuyang (Habukyakjae), gamroang (Jungyakhaesucheop) and chotaekran (Seomseojungyakji). The Lycopus lucidus Turcz has a height of 40 to 100 cm, and its root laterally extends under the ground.

The Lycopus lucidus Turcz contains volatile oils, amino acids, organic acids, glucose, lactose, Lycopus lucidus sugar, saccharose, raffinose, stachyose, fructose and so on, and its fruit contains glucose, lactose, Lycopus lucidus sugar, saccharose, raffinose, hydrogen sugar and so on.

In particular, the Lycopus lucidus Turcz is known to have the effects of removing bruise, activating blood, and removing dropsy and extravasated blood.

According to another embodiment of the present invention, the method for preparing health foods comprising aloeswood according to one aspect of the present invention may further comprise in the preparing a leachate, 3 to 7 parts by weight of black tea leaf, based on 100 parts by weight of the aloeswood and Saururus chinensis mixture.

Here, the black tea leaf is used after washing, drying in shade, pulverizing, and roasting for 1 or 2 minutes in a caldron heated at 90 to 120° C., and then cooling.

The black tea leaf refers to the leaf of black tea that is widely used for drinking in the art. The black tea leaf, providing deep flavors, is widely used as tea.

In particular, the black tea leaf contains a large amount of theaflavin, wherein the theaflavin provides an antioxidant effect, an antibacterial effect, an antineoplastic effect, and an anti-inflammatory effect by removing free radicals, prevents cardiovascular diseases, and helps to prevent lifestyle diseases including cancers.

In addition, a report has shown that when theaflavin extracted from tea was administered to adults having hypercholesteremia with a diet of low saturated fat, the total cholesterol and LDL-cholesterol levels were decreased. It has also been reported that theaflavin was injected to normal cells and colon cancer cells, the normal cells continued to grow but the colon cancer cells underwent apoptosis, which is the natural death of cells. It has also been reported theaflavin extracted from tea prevented colon cancer by inhibiting Cox-2 gene that causes inflammation.

Furthermore, it was shown that the theaflavin contained in black tea has antiviral effects on some viruses, including influenza A and B viruses and hepatitis C virus. Recently, an R&D team of the Chang Gung Memorial Hospital in Chiayi County, Taiwan, published reported that theaflavin has a strong effect of inhibiting the severe acute respiratory syndrome 'coronavirus.'

According to another embodiment of the present invention, the method for preparing health foods comprising aloeswood according to one aspect of the present invention may further comprise in the preparing a leachate, 3 to 7 parts by weight of papaya, based on 100 parts by weight of the aloeswood and Saururus chinensis mixture.

Here, as the method of pretreating aloeswood, Saururus chinensis, Huperzia, white tea and Houttuynia cordata Thunb., the papaya is used after washing, drying in shade, pulverizing, and roasting for 1 or 2 minutes in a caldron heated at 90 to 120° C., and then cooling.

The papaya is an evergreen perennial plant that is assumed to be originally from the tropical region of the Central America. The papaya is distributed in tropical and subtropical regions, and it grows to 1.5 to 3 m in the year of germination, and eventually to 6 to 10 m.

The stem of the papaya becomes thick to a diameter of 20 to 30 cm, but it is not lignified. The stem is empty in the middle, and no branch is generated unless it is pruned. The leaves grow alternately and are concentrated at the top of the stem. The leafstalk is long, and deeply splits into 7 to 9 lines in the form of a palm, like the leaf of fig tree.

According to an article published in the journal 'Ethnopharmacology' by a research group of the University of Florida, the papaya leaf of the papaya has significant effect in treating various cancers, including uterine cancer, breast cancer, liver cancer, lung cancer, pancreatic cancer, and stomach cancer.

Furthermore, a study conducted with cultured cancer cells by using an ingredient extracted from dried papaya leaf showed that when a large amount of papaya tea was injected to cancer cells, a very distinctive anticancer effect was found. This was because the papaya leaf extract not only enhances the production of cytokine, a major signal transmitter of the body, to strengthen the immune system but also has a direct anticancer effect on various cancers, exhibiting an effect of immunotherapy for preventing cancers.

In particular, while other anticancer agents, due to their high toxicity, destroy normal cells as well as cancer cells and causes severe adverse effects such as loss of hair, the papaya leaf, which exhibits anticancer effects through the enhancement of immunity, has almost no adverse effect. When the papaya leaf is combined with a surgery or an anticancer chemotherapy, the therapeutic effect may be elevated.

According to another embodiment of the present invention, the method for preparing health foods comprising aloeswood according to one aspect of the present invention may further comprise in the preparing a leachate, 3 to 7 parts by weight of oriental raisin tree, based on 100 parts by weight of the aloeswood and Saururus chinensis mixture.

Here, the oriental raisin tree is used after washing, drying in shade, pulverizing, and roasting for 1 or 2 minutes in a caldron heated at 90 to 120° C., and then cooling.

The bark, root, leaf, fruit and others of the oriental raisin tree can be used. The oriental raisin tree, a deciduous tall tree of Rhamnaceae Hovenia, contains saccharose, glucose, fructose and catalase, and is widely known to have good effects on intoxication, fever, thirst and hangover.

According to another embodiment of the present invention, the method for preparing health foods comprising aloeswood according to one aspect of the present invention may further comprise in the preparing a leachate, 3 to 7 parts by weight of Rehmannia glutinosa, based on 100 parts by weight of the aloeswood and Saururus chinensis mixture.

Here, the Rehmannia glutinosa is used after washing, drying in shade, pulverizing, and roasting for 1 or 2 minutes in a caldron heated at 90 to 120° C., and then cooling.

The Rehmannia glutinosa may contain the raw roof of Rehmannia glutinosa Liboschitz and Rehmannia glutinosa Libosch.for.hueichingensis Hshlao, which are perennial plants of Serophulariaceae.

The Rehmannia glutinosa may be classified into raw Rehmannia glutinosa and steamed Rehmannia glutinosa, prepared by steaming the raw Rehmannia glutinosa. In the illustrative Examples of the present invention, raw Rehmannia glutinosa is used as the Rehmannia glutinosa, but the application of steamed Rehmannia glutinosa is not excluded.

The ingredients of Rehmannia glutinosa include β-sistosterol, campesterol, rehmanin, alkaloid and fatty acids. The Rehmannia glutinosa has a pharmacological effect of lowering blood sugar level, and acts on the circulatory system to exhibit cardiotonic and diuretic effects. In addition, the Rehmannia glutinosa has an effect of protecting liver functions and an antibacterial effect, inhibiting diabetes, hemoptysis, nosebleed, uterine hemorrhage, menstrual irregularity and constipation.

Hereinafter, the present invention will be described in detail through Examples. However, the following examples are only for illustrating the present invention in detail and are not intended to limit the scope of the present invention by these examples.

Example 1:

Aloeswood, Saururus chinensis, Huperzia, white tea and Houttuynia cordata Thunb. are each washed, and then dried in shade to prepare the materials.

Then, the prepare materials were each put into a pulverizer for pulverizing.

Then, each of the materials prepared as powder was put into a cauldron heated to about 100° C., roasted for 1 minute and 30 second, and cooled to disinfect the materials and enhance the fragrance.

Then, 400 g of aloeswood, 100 g of Saururus chinensis, 100 g of Huperzia, 100 g of white tea and 100 g of Houttuynia cordata Thunb. were mixed with each other, and the resulting mixture was sealed and matured for 5 days.

On the other hand, 50 g of aloeswood and 50 g of Saururus chinensis were mixed with each other to prepare an aloeswood and Saururus chinensis mixture.

Then, 100 g of the aloeswood and Saururus chinensis mixture and 10,000 g (10 L) of water were mixed, and the resulting mixture was boiled at a temperature of about 80° C. for about 24 hours to brew the aloeswood and Saururus chinensis mixture.

Then, the original brewed liquid of the aloeswood and Saururus chinensis mixture was cooled to room temperature and matured at a temperature of about 20° C. for about 24 hours for maturing the brewed aloeswood and Saururus chinensis mixture.

Then, the brewed aloeswood and Saururus chinensis mixture was subject to distilling under reduced pressure under a pressure of 500 mmHg and at a temperature of about 90° C. to obtain a distilled product.

Then, 100 g of the aloeswood and Saururus chinensis mixture that had undergone the distilling under reduced pressure was mixed with 250 g of the mixture that had undergone the maturing an aloeswood, Saururus chinensis, Huperzia, white tea and Houttuynia cordata Thunb. mixture, and the resulting mixture was put into a double boiler and double boiled at a temperature of about 84° C. for about 18 hours to prepare a leachate.

Then, the leachate was put into an extractor and heated at a temperature of about 160° C. for about 13 hours under a pressure of 3.5 kgf/cm$^2$ to perform heat-extraction.

Then, the heat-extracted extract was again put into an extractor and heated under a pressure of 4.2 kgf/cm$^2$ to concentrate.

Then, the concentrated concentrate was heated at a temperature of about 98° C. for about 7 hours to remove moisture from the concentrate for heat-maturing.

Then, the concentrate that had undergone the heat-maturing was dried at a temperature of about 6° C. until the content of moisture became about 15 wt %, and then cooled.

Then, 100 g of the cooled concentrate and 200 g of mineral water were mixed, and the resulting mixture was heated at a temperature of about 95° C. for about 12 minutes, and then dried at room temperature.

Then, the dried concentrate was mixed with 3,000 g of honey, and the resulting mixture was formulated into pills, 2 g for each pill, to prepare a functional food.

Preparation of Adenophola triphylla and Pueraria extraction mixture prepared by mixing Adenophola triphylla and Pueraria extraction at a weight ratio of 1:1

First, 100 g Adenophola triphylla and 100 g of Pueraria were each immersed in water.

Then, 100 g Adenophola triphylla and 100 g of Pueraria were pulled out of water, washed, and then each immersed in water again.

Then, 100 g Adenophola triphylla,100 g of Pueraria and 200 g of water were mixed, and the resulting mixture was heated to boil down until the water is reduced to 100 g.

Then, Adenophola triphylla and Pueraria were pulled out of the water and squeezed to produce a juice.

Then, 100 g of the boiled down water and the juice obtained through the dehydration were mixed, and the resulting mixture was heated at 100° C. for 15 minutes, and cooled to room temperature.

Example 2:

The same method described in Example 1 was implemented, except that 5 g of the Adenophola triphylla and Pueraria extraction mixture prepared by mixing Adenophola triphylla and Pueraria extraction at a weight ratio of 1:1, which was prepared according to [Preparation of Adenophola triphylla and Pueraria extraction mixture prepared by mixing Adenophola triphylla and Pueraria extraction at a weight ratio of 1:1] above, was further added to 100 g of the aloeswood and Saururus chinensis mixture and 250 g of the mixture that had undergone the maturing.

Preparation of cockscomb fermentation product

Cockscomb was pulverized to a size of about 3 mm.

Then, the pulverized cockscomb was mixed with sugar at a weight ratio of 50:40.

Then, after the sugar was sufficiently melt to permeate into the cockscomb mixed with sugar, the resulting mixture was transported to an earthen jar.

Then, the mouth of the earthen jar was covered and sealed with cotton cloth, and the mixture was fermented for 6 months.

Then, solid matters were filtered to prepare a cockscomb fermentation product.

Example 3:

The same method described in Example 1 was implemented, except that 5 g of the cockscomb fermentation product, which was prepared according to [Preparation of cockscomb fermentation product] above, was further added to 100 g of the aloeswood and Saururus chinensis mixture and 250 g of the mixture that had undergone the maturing.

Preparation of enzyme-decomposed tangerine powder

Tangerine was sterilized with a cleaning agent for microbial sterilization and washed with flowing water.

Then, the tangerine was pulverized by using a wet pulverizer with the fruit skin together.

Then, the pulverized tangerine was transported to an enzyme-decomposer in which pectinase was added at a concentration of 200 ppm to perform enzyme-decomposition at 25° C. at a rate of 100 rpm for 3 hours.

Then, the enzyme-decomposed product was separated into juice and flesh by using a filter press, and the flesh was freeze-dried and the pulverized to prepare enzyme- decomposed tangerine powder.

Example 4:

The same method described in Example 1 was implemented, except that 5 g of the enzyme-decomposed tangerine powder, which was prepared according to the preparation of enzyme-decomposed tangerine powder above, was further added to 100 g of the aloeswood and Saururus chinensis mixture and 250 g of the mixture that had undergone the maturing.

Preparation of Dendropanax morbifera leaf powder

Dendropanax morbifera leaf was cleanly washed with water.

Then, the leaf was cut into a size of 1 cm and added to a steamer to steam at 100° C. for 10 minutes.

Then, the leaf was dried in a hot-air dryer at 50° C. for 4 minutes.

Then, the leaf was put into a pulverizer to prepare power.

Example 5:

The same method described in Example 1 was implemented, except that 5 g of the Dendropanax morbifera leaf powder, which was prepared according to [Preparation of Dendropanax morbifera leaf powder] above, was further added to 100 g of the aloeswood and Saururus chinensis mixture and 250 g of the mixture that had undergone the maturing.

Preparation of Poria cocos extract

Poria cocos was cleanly washed with water.

Then, Poria cocos was put into a double boiler to double-boil at a temperature of 80° C. for 18 hours.

Then, the leachate was put into an extractor and heated at a temperature of 150° C. and under a pressure of 4 kgf/cm$^2$ for 12 hours to prepare the extract.

Example 6:

The same method described in Example 1 was implemented, except that 5 g of the Poria cocos extract, which was prepared according to [Preparation of Poria cocos extract] above, was further added to 100 g of the aloeswood and Saururus chinensis mixture and 250 g of the mixture that had undergone the maturing.

Example 7:

The same method described in Example 1 was implemented, except that 10 g of Huperzia serrata was further added to 100 g of the aloeswood and Saururus chinensis mixture and 250 g of the mixture that had undergone the maturing.

Here, the Huperzia serrata was used after washing, drying in shade, pulverizing, roasting for 1 minute and 30 seconds in a caldron heated at 100° C., and then cooling.

Example 8:

The same method described in Example 1 was implemented, except that 8 g of vegetable worm was further added to 100 g of the aloeswood and Saururus chinensis mixture and 250 g of the mixture that had undergone the maturing.

Here, the vegetable worm was used after washing, drying in shade, pulverizing, roasting for 1 minute and 30 seconds in a caldron heated at 100° C., and then cooling.

Example 9:

The same method described in Example 1 was implemented, except that 8 g of Chinese artichoke was further added to 100 g of the aloeswood and Saururus chinensis mixture and 250 g of the mixture that had undergone the maturing.

Here, the Chinese artichoke was used after washing, drying in shade, pulverizing, roasting for 1 minute and 30 seconds in a caldron heated at 100° C., and then cooling.

Example 10:

The same method described in Example 1 was implemented, except that 5 g of Agrimonia eupatoria was further added to 100 g of the aloeswood and Saururus chinensis mixture and 250 g of the mixture that had undergone the maturing.

Here, the Agrimonia eupatoria was used after washing, drying in shade, pulverizing, roasting for 1 minute and 30 seconds in a caldron heated at 100° C., and then cooling.

Example 11:

The same method described in Example 1 was implemented, except that 10 g of Lycopus lucidus Turcz was further added to 100 g of the aloeswood and Saururus chinensis mixture and 250 g of the mixture that had undergone the maturing.

Here, the Lycopus lucidus Turcz was used after washing, drying in shade, pulverizing, roasting for 1 minute and 30 seconds in a caldron heated at 100° C., and then cooling.

Example 12:

The same method described in Example 1 was implemented, except that 5 g of black tea leaf was further added to 100 g of the aloeswood and Saururus chinensis mixture and 250 g of the mixture that had undergone the maturing.

Here, the black tea leaf was used after washing, drying in shade, pulverizing, roasting for 1 minute and 30 seconds in a caldron heated at 100° C., and then cooling.

Example 13:

The same method described in Example 1 was implemented, except that 5 g of papaya was further added to 100 g of the aloeswood and Saururus chinensis mixture and 250 g of the mixture that had undergone the maturing.

Here, the papaya was used after washing, drying in shade, pulverizing, roasting for 1 minute and 30 seconds in a caldron heated at 100° C., and then cooling.

Example 14:

The same method described in Example 1 was implemented, except that 5 g of oriental raisin tree was further added to 100 g of the aloeswood and Saururus chinensis mixture and 250 g of the mixture that had undergone the maturing.

Here, the oriental raisin tree was used after washing, drying in shade, pulverizing, roasting for 1 minute and 30 seconds in a caldron heated at 100° C., and then cooling.

Example 15:

The same method described in Example 1 was implemented, except that 5 g of Rehmannia glutinosa was further added to 100 g of the aloeswood and Saururus chinensis mixture and 250 g of the mixture that had undergone the maturing.

Example 16:

The same method described in Example 1 was implemented, except that 5 g of the Adenophola triphylla and Pueraria extraction mixture prepared by mixing Adenophola triphylla and Pueraria extraction at a weight ratio of 1:1, 5 g of the cockscomb fermentation product, 5 g of the enzyme-decomposed tangerine powder, 5 g of the Poria cocos extract, 5 g of the Dendropanax morbifera leaf powder, 10 g of Huperzia serrata, 8 g of vegetable worm, 8 g of Chinese artichoke, 5 g of Agrimonia eupatoria, 10 g of Lycopus lucidus Turcz, 5 g of black tea leaf, 5 g of papaya, 5 g of oriental raisin tree and 5 g of Rehmannia glutinosa were further added to 100 g of the aloeswood and Saururus chinensis mixture and 250 g of the mixture that had undergone the maturing.

Here, Huperzia serrata, vegetable worm, Chinese artichoke, Agrimonia eupatoria, Lycopus lucidus Turcz, black tea leaf, papaya, oriental raisin tree and so on were used after washing, drying in shade, pulverizing, roasting for 1 minute and 30 seconds in a caldron heated at 100° C., and then cooling.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention. The scope of the present invention is defined by the appended claims rather than the detailed description and all changes or modifications derived from the meaning and scope of the claims and their equivalents should be construed as being included within the scope of the present invention.

What is claimed is:

1. A method for preparing health foods comprising aloeswood, the method comprising:
    preparing materials in which aloeswood, Saururus chinensis, Huperzia, white tea and Houttuynia cordata Thunb are each washed, and then dried in shade;
    pulverizing in which, after the preparing materials is completed, each material is pulverized by using a pulverizer;
    roasting in which, after the pulverizing is completed, each pulverized material is roasted in a cauldron heated to 90 to 120° C. for 1 to 2 minutes to sterilize the materials and enhance fragrances, and then cooled;
    maturing an aloeswood, Saururus chinensis, Huperzia, white tea and Houttuynia cordata Thunb mixture in which, after the roasting is completed, the roasted aloeswood, Saururus chinensis, Huperzia, white tea and Houttuynia cordata Thunb are mixed at a weight ratio of 4:1:1:1:1 and then sealed in an earthen jar and matured for 6 to 8 days;
    preparing an aloeswood and Saururus chinensis mixture in which a mixture is prepared by mixing aloeswood and Saururus chinensis at a weight ratio of 1:1;
    brewing in which the aloeswood and Saururus chinensis mixture is added, based on 100 parts by weight of the aloeswood and Saururus chinensis mixture, to 4,000 to 12,000 parts by weight of water, and then heated at a temperature range of 70 to 90° C. for 22 to 26 hours;
    maturing the aloeswood and Saururus chinensis mixture in which, after the brewing is completed, the aloeswood and Saururus chinensis mixture is cooled to room temperature and then matured at a temperature range of 18 to 22° C. for 22 to 26 hours;
    distilling under reduced pressure in which, after the maturing the aloeswood and Saururus chinensis mixture is completed, distilling under reduced pressure is performed;
    preparing a leachate in which the aloeswood and Saururus chinensis mixture that has undergone the distilling under reduced pressure is mixed with the mixture that has undergone the maturing an aloeswood, Saururus chinensis, Huperzia, white tea and Houttuynia cordata Thunb. mixture at a weight ratio of 1:1 to 1:3, and the resulting mixture is put into a double boiler and heated at a temperature range of 83 to 85° C. for 15 to 20 hours to prepare a leachate;
    extracting in which, after the preparing a leachate is completed, the prepared leachate is put into an extractor and heated at a temperature range of 150 to 180° C. for 10 to 15 hours under a pressure of 3 to 4 $kgf/cm^2$ to extract;
    concentrating in which an extract obtained after the extracting is completed is put into the extractor again and heated under a pressure of 4 to 4.5 $kgf/cm^2$ for 2 to 4 hours to concentrate the extract;
    heat-maturing in which a concentrate obtained after the concentrating is completed is heated at a temperature range of 95 to 100° C. for 6 to 8 hours to mature the concentrate by removing moisture;
    cool-drying the concentrate in which the concentrate obtained after the heat-maturing is completed is dried at a temperature range of 5 to 8° C. until the moisture content becomes 14 to 16 wt %;
    heating the concentrate in which the concentrate that has undergone the cool-drying of a concentrate is put into, based on 100 parts by weight of the concentrate, 100 to 300 parts by weight of mineral water, and then heated at a temperature range of 90 to 98° C. for 5 to 20 minutes;
    drying the concentrate in which the concentrate, after the heating the concentrate is completed, is dried at room temperature; and
    molding in which the concentrate, after the drying the concentrate is completed, is molded to a predetermined shape.

2. The method for preparing health foods comprising aloeswood according to claim 1, the method further comprising preparing a concentrate and honey mixture, following the drying the concentrate, in which the dried concentrate is mixed with, based on 100 parts by weight of the concentrate, 2,500 to 3,500 parts by weight of honey.

3. The method for preparing health foods comprising aloeswood according to claim 1, wherein the pulverizing is performed such that each material has an a mean diameter in a range of 0.1 to 3.0 mm.

4. The method for preparing health foods comprising aloeswood according to claim 1, wherein the aloeswood in the preparing materials comprises aloeswood generated by the solidification of resin of aloeswood trees.

* * * * *